United States Patent
Cohn

(10) Patent No.: US 8,636,660 B1
(45) Date of Patent: Jan. 28, 2014

(54) SYSTEM AND METHOD FOR DYNAMIC MULTI-STAGE TEST ADMINISTRATION FOR DETECTION OF CARDIOVASCULAR DISEASE

(71) Applicant: Jay N. Cohn, Minneapolis, MN (US)

(72) Inventor: Jay N. Cohn, Minneapolis, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 0 days.

(21) Appl. No.: 13/648,168

(22) Filed: Oct. 9, 2012

(51) Int. Cl.
    *A61B 5/00* (2006.01)

(52) U.S. Cl.
    USPC .......................................... 600/301; 600/509

(58) Field of Classification Search
    None
    See application file for complete search history.

(56) References Cited

U.S. PATENT DOCUMENTS

| | | | |
|---|---|---|---|
| 5,054,493 A | 10/1991 | Cohn et al. | |
| 5,396,886 A | 3/1995 | Cuypers | |
| 6,110,109 A | 8/2000 | Hu et al. | |
| 6,322,504 B1 | 11/2001 | Kirshner | |
| 6,331,161 B1 | 12/2001 | Chesney et al. | |
| 2004/0026185 A1 | 2/2004 | Murayama et al. | |
| 2005/0273359 A1* | 12/2005 | Young | 705/2 |
| 2007/0060821 A1 | 3/2007 | Cohn | |
| 2007/0168308 A1* | 7/2007 | Wang et al. | 706/20 |
| 2008/0171916 A1* | 7/2008 | Feder et al. | 600/300 |
| 2009/0036748 A1* | 2/2009 | Pergament et al. | 600/300 |
| 2010/0094648 A1* | 4/2010 | Seward | 705/2 |
| 2010/0217094 A1* | 8/2010 | Seward | 600/300 |
| 2011/0029322 A1* | 2/2011 | Hindo et al. | 705/2 |

OTHER PUBLICATIONS

Duprez, D. A., "Identifying Early Cardiovascular Disease to Target Candidates for Treatment", *The Journal of Clinical Hypertension*, 10(3), (Mar. 2008), 226-231.

Duprez, D. A, et al., "Vascular and cardiac functional and structural screening to identify risk of future morbid events: preliminary observations", *Journal of the American Society of Hypertension*, 5(5), (2011), 401-409.

"U.S. Appl. No. 10/372,001, Non Final Office Action mailed Apr. 7, 2006", 7 pgs.

"U.S. Appl. No. 10/372,001, Non Final Office Action mailed Sep. 20, 2005", 8 pgs.

"U.S. Appl. No. 10/372,001, Response filed Dec. 20, 2005 to Non Final Office Action mailed Sep. 20, 2005", 13 pgs.

"U.S. Appl. No. 11/545,812, Appeal Brief filed Jul. 5, 2011", 24 pgs.

"U.S. Appl. No. 11/545,812, Advisory Action mailed Dec. 7, 2010", 6 pgs.

"U.S. Appl. No. 11/545,812, Examiner Interview Summary mailed Jul. 19, 2010", 3 pgs.

"U.S. Appl. No. 11/545,812, Examiner's Answer to Appeal Brief mailed Oct. 5, 2011", 10 pgs.

(Continued)

*Primary Examiner* — Bill Thomson
*Assistant Examiner* — Davin K Sands
(74) *Attorney, Agent, or Firm* — Schwegman, Lundberg & Woessner, P.A.

(57) ABSTRACT

A system and method for dynamic multi-stage test administration for detection of cardiovascular disease may include performing a first set of tests in a first stage of testing on a patient. Physiological results for each of the tests in the first stage may then be received. Then, based on the physiological results, dynamically determining a set of tests to perform on the subject in a second stage of testing. Additionally, the dynamically determined set of tests in the second stage of testing may be performed on the subject.

16 Claims, 9 Drawing Sheets

(56) References Cited

OTHER PUBLICATIONS

"U.S. Appl. No. 11/545,812, Final Office Action mailed Jul. 13, 2009", 9 pgs.
"U.S. Appl. No. 11/545,812, Final Office Action mailed Sep. 30, 2010", 6 pgs.
"U.S. Appl. No. 11/545,812, Non-Final Office Action mailed Dec. 23, 2009", 9 pgs.
"U.S. Appl. No. 11/545,812, Non-Final Office Action mailed Dec. 24, 2008", 12 pgs.
"U.S. Appl. No. 11/545,812, Preliminary Amendment filed Jan. 4, 2007", 14 pgs.
"U.S. Appl. No. 11/545,812, Reply Brief filed Dec. 5, 2011", 3 pgs.
"U.S. Appl. No. 11/545,812, Response filed Apr. 24, 2009 to Non Final Office Action mailed Dec. 24, 2009", 14 pgs.
"U.S. Appl. No. 11/545,812, Response filed Jun. 23, 2010 to Non Final Office Action mailed Dec. 23, 2009", 8 pgs.
"U.S. Appl. No. 11/545,812, Response filed Oct. 13, 2009 to Final Office Action mailed Jul. 13, 2009", 10 pgs.
"U.S. Appl. No. 11/545,812, Response filed Nov. 30, 2010 to Final Office Action mailed Sep. 30, 2010", 9 pgs.
"U.S. Appl. No. 11/545,812, Supplemntal Response to Non Final Office Action mailed Dec. 23, 2009", 7 pgs.
Anonymous, "Effect of enalapril on mortality and the development of heart failure in asymptomatic patients with reduced left ventricular ejection fractions. The SOLVD Investigators", New England Journal of Medicine, 327(10), (Sep. 3, 1992), 685-91.
Anonymous, "Prevention of cardiovascular events and death with pravastatin in patients with coronary heart disease and a broad range of initial cholesterol levels. The Long-Term Intervention with Pravastatin in Ischaemic Disease (LIPID) Study Group", New England Journal of Medicine, 339(19), (Nov. 5, 1998), 1349-57.
Anonymous, "Randomised trial of cholesterol lowering in 4444 patients with coronary heart disease: the Scandinavian Simvastatin Survival Study", Lancet, 344(8934), (Nov. 19, 1994), 1383-9.
Anonymous, "Secondary prevention of vascular disease by prolonged antiplatelet treatment. Antiplatelet Trialists' Collaboration", British Medical Journal, 296(6618), (Jan. 30, 1988), 320-31.
Beevers, D. G, et al., "Hypertension in Practice", Informa Health Care, (1999).
Borch-Johnsen, K, et al., "Urinary albumin excretion. An independent predictor of ischemic heart disease", Arteriosclerosis, Thrombosis & Vascular Biology, 19(8), (Aug. 1999), 1992-7.
Clarke, R, et al., "Hyperhomocysteinemia: an independent risk factor for vascular disease", New England Journal of Medicine, 324(17), (Apr. 25, 1991), 1149-55.
Cohn, J N, "Arteries, myocardium, blood pressure and cardiovascular risk: towards a revised definition of hypertension", Journal of Hypertension, 16(12 Pt 2), (Dec. 1998), 2117-24.
Cohn, J. N., "Noninvasive pulse wave analysis for the early detection of vascular disease", Hypertension, 26(3), (Sep. 1995), 503-508.
Downs, S L, et al., "Primary prevention of acute coronary events with lovastatin in men and women with average cholesterol levels: results of AFCAPS/TexCAPS. Air Force/Texas Coronary Atherosclerosis Prevention Study", JAMA, 279(20), (May 27, 1998), 1615-22.
Gottlieb, S S, et al., "Effect of beta-blockade on mortality among high-risk and low-risk patients after myocardial infarction", New England Journal of Medicine, 339(8), (Aug. 20, 1998), 489-97.
Grundy, S M, et al., "Primary prevention of coronary heart disease: guidance from Framingham: a statement for healthcare professionals from the AHA Task Force on Risk Reduction. American Heart Association", Circulation, 97(18), (May 12, 1998), 1876-87.
Hirsch, A T, et al., "Peripheral arterial disease detection, awareness, and treatment in primary care", JAMA, 286(11), (Sep. 19, 2001), 1317-24.
Kannel, William B, "Blood pressure as a cardiovascular risk factor: prevention and treatment", JAMA, 275(20), (May 22-29, 1996), 1571-6.
Lim, P, et al., "Dundee step test: a simple method of measuring the blood pressure response to exercise", Journal of Human Hypertension, 13(8), (Aug. 1999), 521-6.
Maisel, A S, "Utility of B-natriuretic peptide as a rapid, point-of-care test for screening patients undergoing echocardiography to determine left ventricular dysfunction", American Heart Journal, 141(3), (Mar. 2001), 367-74.
MERIT-HF Study Group, "Effect of metoprolol CR/XL in chronic heart failure: Metoprolol CR/XL Randomised Intervention Trial in Congestive Heart Failure (MERIT-HF)", Lancet, 353(9169), (Jun. 12, 1999), 2001-7.
Ridker, P M, et al., "C-reactive protein adds to the predictive value of total and HDL cholesterol in determining risk of first myocardial infarction", Circulation, 97(20), (May 26, 1998), 2007-11.
Ross, R, "The pathogenesis of atherosclerosis: a perspective for the 1990s", Nature, 362(6423), (Apr. 29, 1993), 801-9.
Stein, J H, et al., "Lipoprotein Lp(a) excess and coronary heart disease", Archives of Internal Medicine, 157(11), (Jun. 9, 1997), 1170-6.
Yusuf, S, et al., "Effects of an angiotensin-converting-enzyme inhibitor, ramipril, on cardiovascular events in high-risk patients. The Heart Outcomes Prevention Evaluation Study Investigators", New England Journal of Medicine, 342(3), (Jan. 20, 2000), 145-53.

* cited by examiner

Figure 1
Range of Values of Arterial Elasticity Measurement

| Age Catergory (years) | Gender | C1 (capacitive) (ml/mmHgx10) | | | C2 (oscillatory) (ml/mmHgx100) | | |
|---|---|---|---|---|---|---|---|
| | | Normal | Borderline | Abnormal | Normal | Borderline | Abnormal |
| ≤45 | male | ≥15.0 | 13.0 – 14.9 | <13.0 | ≥7.0 | 6.0 – 6.9 | <6.0 |
| | female | ≥14.0 | 12.0 – 13.9 | <12.0 | ≥6.0 | 5.0 – 5.9 | <5.0 |
| 46-54 | male | ≥13.0 | 11.0 – 12.9 | <11.0 | ≥6.0 | 5.0 – 5.9 | <5.0 |
| | female | ≥12.0 | 10.0 – 11.9 | <10.0 | ≥5.0 | 4.0 – 4.9 | <4.0 |
| 55-64 | male | ≥12.0 | 10.0 – 11.9 | <10.0 | ≥5.0 | 4.0 – 4.9 | <4.0 |
| | female | ≥11.0 | 9.0 – 10.9 | <9.0 | ≥4.0 | 3.5 – 3.9 | <3.5 |
| 65-74 | male | ≥11.0 | 9.0 – 10.9 | <9.0 | ≥4.5 | 4.0 – 4.4 | <4.0 |
| | female | ≥10.0 | 9.0 – 9.9 | <9.0 | ≥3.5 | 3.0 – 3.4 | <3.0 |
| ≥75 | male | ≥10.0 | 9.0 – 9.9 | <9.0 | ≥4.0 | 3.5 – 3.9 | <3.5 |
| | female | ≥9.5 | 8.5 – 9.4 | <8.5 | ≥3.0 | 2.5 – 2.9 | <2.5 |

Figure 2

| Test | Normal | Borderline | Abnormal |
|---|---|---|---|
| Arterial Elasticity | See Figure 1 | | |
| Resting blood pressure (mmHg) | SBP <130 and DBP <85 | SBP 130-139 or DBP 85-89 | SBP ≥140 Or DBP ≥90 |
| Exercise blood pressure (mmHg) | SBP rise <30 and SBP ≤169 | SBP rise 30-39 or SBP 170-179 | SBP rise ≥40 or SBP ≥180 |
| Optic fundus | A:V ratio >3:5 | A:V ratio ≤3:5 or Mild A:V crossing changes | A:V ratio ≤1:2 or A:V nicking |
| Microalbuminuria (mg/mmol) | <0.6 | 0.61-0.99 | ≥1.00 |
| Ankle-brachial index | >0.90 | — | <0.90 |
| Electrocardiogram | No abnormalities | Non-Specific Abnormality | Diagnostic abnormality |
| LV Ultrasound | LVIDD/BSA <2.70 cm And LVM/BSA <120 gm | 2.70-2.89 cm or 120-129 gm | ≥2.9 cm or ≥130 gm |
| BNP (pg/dl) | <50 | 51-99 | ≥100 |

| Laboratory Test | | Reference Range | | | Units |
|---|---|---|---|---|---|
| | | Optimal | Borderline | Abnormal | |
| HDL-C | HDL Cholesterol | ≥ 45 men<br>≥ 55 women | 40-45 men<br>50-55 women | ≤ 40 men<br>≤ 50 women | mg/dL |
| LDL-C | LDL Cholesterol | ≤ 100 | 101-129 | ≥ 130 | mg/dL |
| TG | Triglycerides | ≤ 150 | 151-199 | ≥ 200 | mg/dL |
| GLUC | Glucose | ≤ 100 | 111-125 | ≥ 126 | mg/dL |
| HsCRP | C-Reactive Protein | ≤ 0.300 | | > 0.300 | mg/dL |

Figure 3
Disease Contributors

Figure 4
Demographics of Population

|  | No Events<br>n = 578 | Events<br>n = 35 | P-Value |
|---|---|---|---|
| Age (years) | 53.7 ± 10.7 | 61.6 ± 8.1 | <.001 |
| % women | 45.9 ± 49.9 | 25.7 ± 44.3 | 0.020 |
| BMI (kg/m$^2$) | 27.2 ± 5.2 | 27.8 ± 3.5 | 0.504 |
| Total Cholesterol (mg/dl) | 204.0 ± 40.7 | 194.7 ± 38.6 | 0.191 |
| LDL Cholesterol (mg/dl) | 127.3 ± 37.0 | 123.8 ± 32.0 | 0.584 |
| HDL Cholesterol (mg/dl) | 51.3 ± 16.2 | 47.6 ± 13.2 | 0.184 |
| Log Triglycerides | 4.7 ± 0.5 | 4.6 ± 0.5 | 0.227 |
| Glucose (mg/dl) | 93.8 ± 16.2 | 97.9 ± 13.9 | 0.149 |
| hs-CRP (mg/dL) | 0.3 ± 0.7 | 0.4 ± 0.6 | 0.595 |
| Framingham Risk Score | 10.3 ± 4.7 | 12.7 ± 2.6 | 0.003 |
| Rasmussen Score | 4.6 ± 3.2 | 7.3 ± 2.8 | <.001 |

BMI: body mass index; hs-CRP: high sensitivity C-reactive protein

Figure 5
Assessment of Early Cardiovascular Disease

| Measure | Events n = 35 | No Events n = 578 | p value |
|---|---|---|---|
| Variables contributing to score | | | |
| Large artery elasticity (mL/mm Hg x 10) | 16.2 ± 6.5 | 16.7 ± 5.7 | .581 |
| Small artery elasticity (mL/mm Hg x 100) | 5.0 ± 2.7 | 6.2 ± 3.1 | .024 |
| Resting systolic blood pressure (mm Hg) | 132.2 ± 16.6 | 126.6 ± 16.6 | .053 |
| Resting diastolic blood pressure (mm Hg) | 79.9 ± 10.9 | 79.0 ± 9.9 | .617 |
| Change in systolic blood pressure (mm Hg) | 25.2 ± 19.3 | 23.6 ± 15.6 | .559 |
| Change in diastolic blood pressure (mm Hg) | -8.9 ± 9.9 | -10.1 ± 8.8 | .430 |
| Left ventricular mass index (g/m$^2$) | 87.1 ± 24.7 | 73.7 ± 18.9 | <.001 |
| Micoalbuminuria (mg/mmoL) | 2.3 ± 8.2 | 0.9 ± 2.2 | .007 |
| B-type natriuretic peptide (pg/dL) | 99.4 ± 133.3 | 59.5 ± 73.4 | .003 |
| Retinal score | 1.1 ± 0.9 | 0.6 ± 0.7 | <.001 |
| Carotid ultrasound score | 0.9 ± 0.9 | 0.5 ± 0.8 | .014 |
| Eletrocardiogram score | 0.9 ± 1.0 | 0.2 ± 0.6 | <.001 |

Figure 6
Risk Factors in Three Disease Score Groups

|  | Disease Scores | | | p value |
|---|---|---|---|---|
|  | 0-2 (n = 169) | 3-5 (n = 214) | 6+ (n = 230) |  |
| Age (years) | 48.6 ± 10.2 | 53.3 ± 9.5 | 59.0 ± 9.9 | <.001 |
| % women | 42.3 ± 49.5 | 41.6 ± 49.4 | 49.6 ± 50.1 | .180 |
| Body mass index (kg/m$^2$) | 26.5 ± 4.4 | 27.4 ± 5.4 | 27.6 ± 5.3 | .078 |
| Total cholesterol (mg/dL) | 199.3 ± 36.1 | 201.3 ± 39.2 | 208.6 ± 44.6 | .049 |
| Low-density lipoprotein cholesterol (mg/dL) | 123.8 ± 32.0 | 126.8 ± 37.4 | 129.8 ± 39.2 | .281 |
| High-density lipoprotein cholesterol (mg/dL) | 50.3 ± 15.1 | 50.4 ± 16.0 | 52.3 ± 16.9 | .342 |
| Log triglycerides | 4.7 ± 0.5 | 4.7 ± 0.5 | 4.8 ± 0.6 | .349 |
| Glucose (mg/dL) | 92.7 ± 14.6 | 93.4 ± 19.3 | 95.6 ± 13.7 | .176 |
| C-reactive protein (mg/dL) | 0.3 ± 0.6 | 0.3 ± 0.7 | 0.4 ± 0.6 | .387 |

SYSTEM AND METHOD FOR DYNAMIC MULTI-STAGE TEST ADMINISTRATION FOR DETECTION OF CARDIOVASCULAR DISEASE

RELATED APPLICATIONS

This application is a related to U.S. patent application Ser. No. 11/545,812, filed Oct. 10, 2006, which claims priority from U.S. Provisional Application No. 60/359,117, filed 21 Feb. 2002; which applications are incorporated by reference herein.

TECHNICAL FIELD OF THE INVENTION

The present invention relates generally to the field of medicine and more particularly, to diagnosis, monitoring, and treatment of disease.

BACKGROUND OF THE INVENTION

Most preventive efforts nationally have been devoted to risk factor modification in the asymptomatic population (primary prevention)[1,2] or intervention in individuals who have sustained cardiovascular morbid events (secondary prevention).[3-6] Little attention has been directed to the recognition of early abnormalities of vascular and cardiac function or structure, which are always detectable before symptomatic organ involvement has occurred. Risk factor modification is aimed at preventing progression of disease but can have no benefit in individuals who do not have vascular or cardiac abnormalities and are not at risk for a premature cardiovascular event. Furthermore, cardiovascular disease often exists and progresses in the absence of the traditional risk markers and its course can still be altered by intervention. Focusing on risk factor identification and management alone is doomed to insensitivity and non-specificity in achieving risk reduction, whereas focusing on individuals with advanced disease will not accomplish the desired goal of symptomatic disease prevention and health care cost reduction.

Risk markers such as age, blood pressure, cholesterol levels, blood sugar, homocysteine and inflammatory markers may correlate with the risk of cardiovascular events[7-1], much as the barometer may predict the likelihood of rain, but the first few raindrops are a far more sensitive and specific marker for raising the umbrella. Since potent interventions are now available to slow the progression of cardiovascular disease,[11-13] the need has increased for techniques that can identify the earliest markers for the disease rather than the risk. Such data might allow the application of a much more targeted approach to the prevention of first events in asymptomatic individuals.

A community testing and screening center was used to screen ostensibly healthy individuals in the Twin Cities community for detection of early markers for vascular and cardiac disease. A comprehensive array of non-invasive testing was developed using techniques that have either been established or advocated for early detection. In addition we undertook measurement of modifiable risk contributors that could serve to steer interventions in those with markers for disease.

As described in application Ser. No. 11/545,812, titled "SCREENING FOR EARLY DETECTION OF CARDIOVASCULAR DISEASE IN ASYMPTOMATIC INDIVIDUALS" a novel system for testing asymptomatic individuals for cardiovascular functional or structural abnormalities was described to address the above concerns. The system utilized a series of ten tests that were individually scored (e.g., a ranking selected from 0, 1, or 2) and totaled (e.g., 0-20 possible range) to provide an indication markers for early vascular and cardiac disease.

SUMMARY

The system described above has led to further improvements in order to increase the efficiency of the evaluation. In an embodiment, a version of the original system required all subjects to undergo all 10 tests, which required an hour and a skilled technologist. As described herein, it has been documented that 4 of the tests, which can be performed in 10-15 minutes by a less-skilled technician, can identify 60% of the population who are unlikely to have abnormalities that place them at risk. Thus, the preliminary screening can limit the full 10-test evaluation to the 40% of the population at highest risk for early disease. This in turn leads to the ability to screen larger groups of people for early markers for vascular and cardiac disease. Reducing the number of tests also has the benefit of reducing the costs of population screening.

The description herein describes various embodiment to reduce the number of tests needed to determine if an individual shows early markers for vascular and cardiac disease. In an embodiment, a dynamic multi-stage test administration is used for detection of cardiovascular disease.

In one example, a group of 1806 asymptomatic individuals were evaluated using the ten test procedure. Each individual was given an overall disease score based on the total of individual scores for each test as described herein. Additionally, a score was determined for the four tests consisting of the measurement of resting blood pressure, the measurement of the change in blood pressure in response to 3 minutes of exercise on a treadmill adjusted for a work load of 5 METS (metabolic equivalents), and measurement of small artery and large artery elasticity with a transducer applied to the wrist.

Analyzing this data revealed that 1103 (61%) of this population had scores on the four-test screen of less than 3. Only 10% of this group had Disease Scores higher than 6 requiring treatment. Of the 703 individuals (39%) with 4-test scores of 3 or greater, 73% of them had Disease Scores greater than 6 and in need of therapy to slow progression of their disease. Thus, the four-test screening therefore makes it possible to exclude more than 60% of the population from the need for a full evaluation. This greatly facilitates the effort to screen the entire population for early disease to eliminate heart attacks and strokes.

BRIEF DESCRIPTION OF THE DRAWINGS

FIG. 1 is a tabular view of a range of values of arterial elasticity measurement, according to an example embodiment.

FIG. 2 is a tabular view of a range of values of markers for cardiovascular disease, according to an example embodiment.

FIG. 3 is a tabular view of laboratory test disease contributors, according to an example embodiment.

FIG. 4 displays demographic data in 613 individuals studied, 35 who during up to 6 years of follow-up sustained a cardiovascular morbid event and 578 who did not, according to an example embodiment.

FIG. 5 provides data on the 10-test study results in the two groups of individuals discussed in FIG. 4, according to an example embodiment. Systolic and diastolic pressures are displayed separately but are included as single tests.

FIG. 6 displays the traditional risk factors in 3 groups of individuals classified by their Disease Scores, according to an example embodiment.

DETAILED DESCRIPTION OF THE INVENTION

Figure 7:
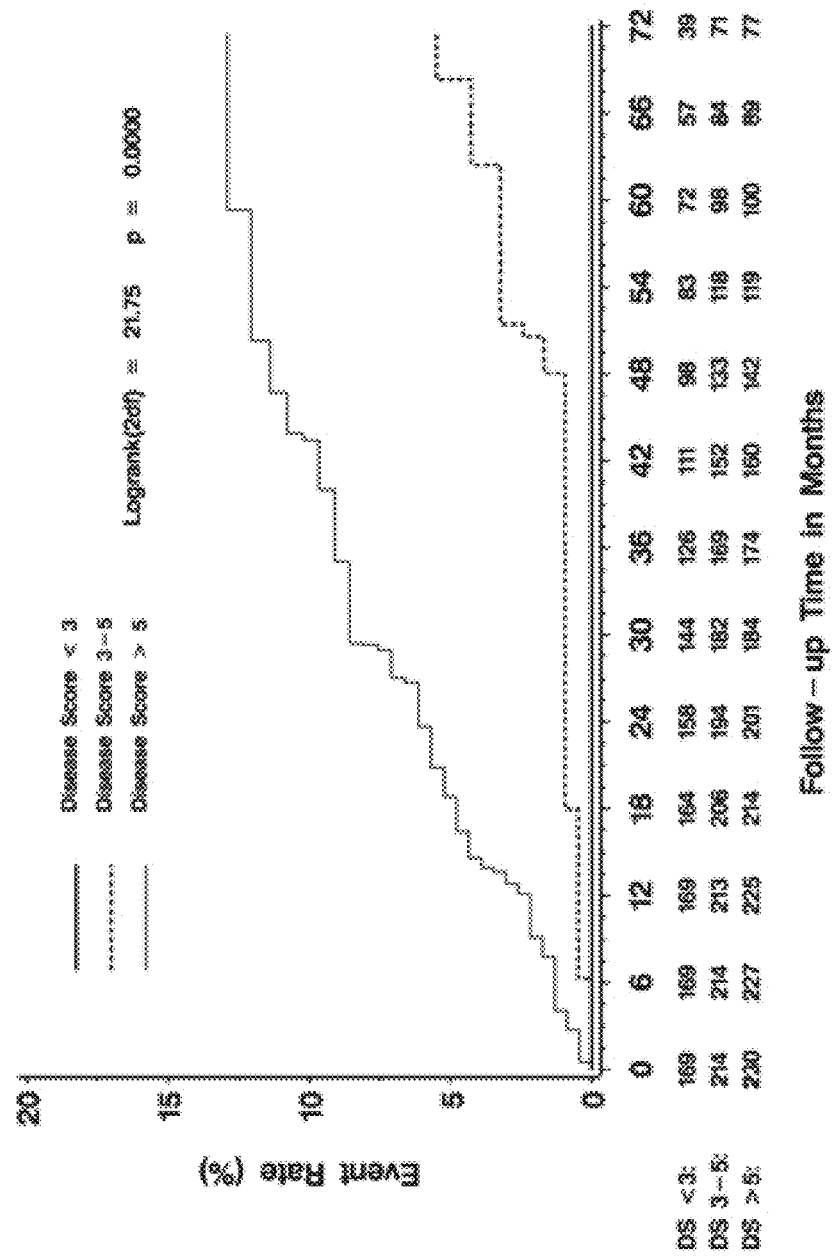
FIG. 7 displays Kaplan Meier curves for the risk for morbid events during 6 years of follow-up of individuals with Disease Scores of 0-2, 3-5 and over 6, according to an example embodiment.

The following detailed description includes references to the accompanying drawings, which form a part of the detailed description. The drawings show, by way of illustration, specific embodiments in which the invention may be practiced. These embodiments, which are also referred to herein as "examples," are illustrated in enough detail to enable those skilled in the art to practice the invention. The embodiments may be combined, other embodiments may be utilized, or structural, logical, and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Methods

The history, physical examination and laboratory testing in the testing and screening center are carried out by a nurse practitioner with staff under her direction. Physician oversight includes chart and data review, report generation and, only when indicated, direct patient contact.

Early Disease Assessment

The screening tests employed are designed to separately assess early markers for arterial and left ventricular disease.

Arterial Abnormalities:

Since endothelial dysfunction may be the earliest manifestation of arterial disease likely to progress to symptomatic atherosclerosis[14], the goal has been to assess early markers for endothelial and vascular dysfunction in an attempt to identify disease that has not become symptomatic. The following tests are employed:

1. Arterial elasticity. Pulse contour analysis allows separate assessment of the elasticity of the large conduit arteries and the small arteries that serve as sites of reflected waves in the circulation. A pulse wave analysis methodology developed at the University of Minnesota and now commercially marketed (Hypertension Diagnostics, Inc. Eagan, Minn.) is utilized. The methodology includes applying a piezoelectric transducer to a radial artery with on-line computer analysis of the pulse wave with a rapid printout of a cardiovascular profile that includes large artery elasticity ($C_1$) and small artery elasticity ($C_2$). Previous studies have validated the methodology, demonstrated the decline in $C_1$ and $C_2$ with aging, demonstrated abnormally low $C_2$ levels in patients with cardiovascular disease, and shown a correlation between risk factors for cardiovascular disease and a low $C_2$.[15]

2. Blood pressure at rest and during exercise. A standardized 3-minute treadmill exercise test at a 5 met workload is performed to monitor the rise in systolic blood pressure with exercise. A brisk rise has previously been shown to correlate with reduced arterial elasticity or compliance.[16]

3. Optic fundus photos. A digital camera (Canon, Greenville, S.C.) is used to image the optic fundus without the need for mydriasis. Fundus photos are analyzed for the A:V ratio and the presence of A:V crossing changes.

4. Microalbuminuria. A spot urine sample is analyzed for the albumin excretion per mg creatinine, a marker for small artery disease in the kidney.[17]

5. Carotid Artery Ultrasound). An ultrasound probe is placed over both carotid arteries to measure artery wall thickness (intimal-medial thickness) and the presence of atherosclerotic plaques[18]

Cardiac Abnormalities:

Left ventricular abnormalities precede the onset of symptoms of cardiac dysfunction. Identification of early cardiac disease could allow intervention that may be effective in slowing progression.[11]

1. Electrocardiogram (high-risk only).
2. Left ventricular (LV) ultrasound. A hand-held portable echocardiographic unit (Sonosite, Bothell, Wash.) is used to screen the left ventricle for transverse diameter and wall thickness.
3. Plasma NT-Pro BNP concentration. Brain natriuretic peptide levels are a sensitive guide to left ventricular dysfunction.[19] A blood sample is collected for laboratory determination of NT-ProBNP levels.

Scoring System

Each of the tests employed is categorized as normal or abnormal. In some instances a borderline abnormal range is identified. The ranges assigned to each test are shown in FIGS. 1 and 2. An abnormal test contributes 2 points to an overall disease assessment score, a borderline test 1 point and a normal test 0. The overall score (range 0 to 20) provides a continuum from no disease to severe disease.

Modifiable Disease Contributors

When early disease is present, identification and aggressive treatment of modifiable factors that contribute to disease progression is mandatory. When disease is not present, modest life-style interventions to lower the risk of future disease development may still be prudent.

1. Blood pressure. Taken seated at rest.
2. Fasting lipid levels. Patients are instructed to come to the center fasting and blood is drawn for analysis of cholesterol, LDL, HDL and triglycerides.
3. Fasting blood sugar.
3. C-reactive protein. This inflammatory marker is associated with the risk of atherosclerotic events.

The results of some of these tests are divided into optimal, borderline and abnormal, with abnormal results clear targets for therapy and borderline tests optional targets, depending on the evidence for cardiovascular disease, as shown in FIG. 3.

Results

The demographics of 613 individuals without known cardiovascular disease who were tested in the Minneapolis/St.

Paul, Minn., area, whose results have been entered into the database and whose outcome has been assessed for more than 6 months, are shown in FIG. 4. Those who subsequently during follow-up suffered from a morbid cardiovascular event (n=35) are identified as the Event group and those (n=578) who did not experience a morbid cardiovascular event are identified as the No Event group.[20]

Our testing procedures appeared effective in identifying pre-clinical vascular and cardiac disease that mandated initiation or change in medical therapy. The evidence for vascular and cardiac disease in the Event and No Event groups is summarized in FIG. 5. The Disease Scores in individual patients were divided into 3 nearly equal groups: those with scores of 0-2, 3-5 and 6 or greater. The traditional risk factors in these 3 groups are shown in FIG. 6. Note that most of the traditional risk factors are not effective in distinguishing between those individuals with no disease (scores 0-2), early disease (scores 3-5) and advancing disease (scores of 6 or greater). None of these risk factors were effective in identifying those with advanced disease.

The predictive value of the Disease Score in identifying those who will subsequently suffer a cardiovascular morbid event is displayed in FIG. 7, according to an embodiment. Kaplan-Meier curves reveal no morbid events for 6 years in the no disease group (scores 0-2), events beginning after 4 years in the early disease group (scores 3-5) and events beginning immediately in the advanced disease group (scores 6 or greater). Thus, the low Disease Score group had no morbid events and the high Disease Score group experienced early and frequent morbid events. The intermediate Disease Score group had delayed onset of morbid events.[20]

Figure 8:
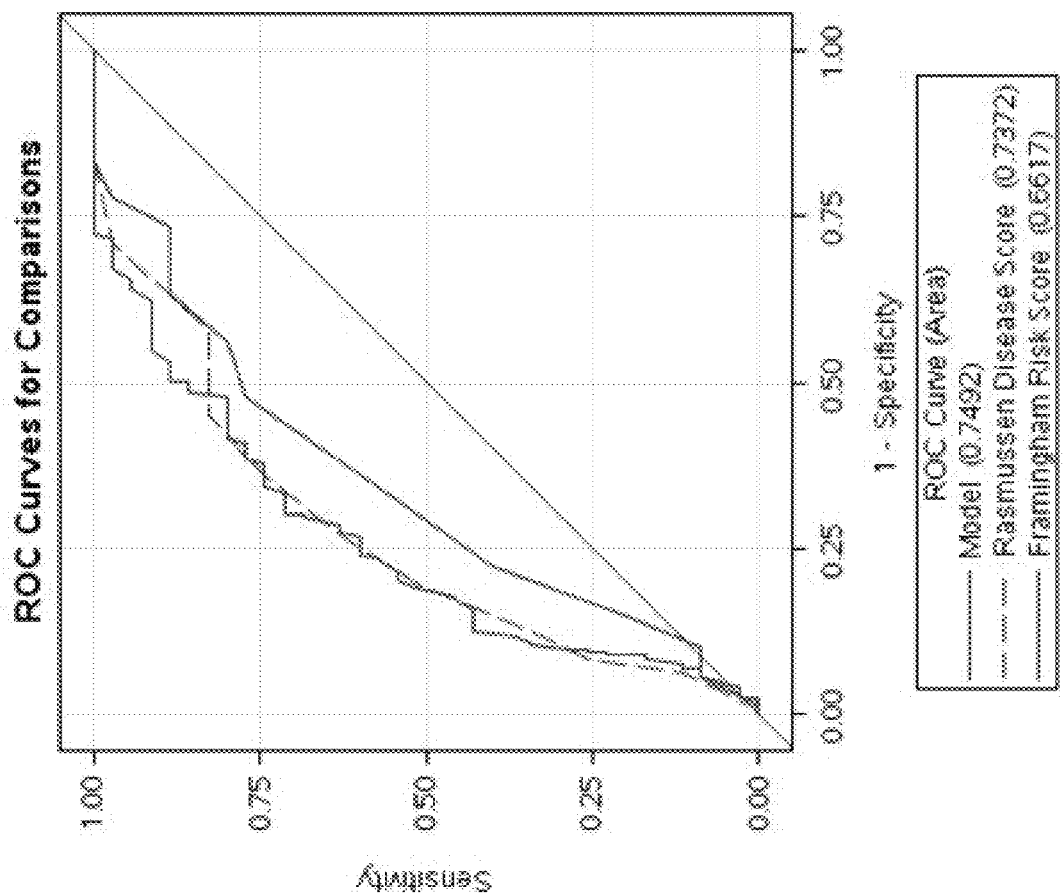
FIG. 8 shows receiver operating curves for sensitivity and specificity of the Disease Score compared to the Framingham Risk Score, according to an example embodiment.

The discriminatory value of the Disease Score compared to the traditional Framingham Risk Score was evaluated by constructing receiver operating characteristics curves. As shown in FIG. 8 the area under the curve for the Disease Score significantly surpassed the area for the Risk Score, and adding the two together in a model did not improve on the Disease Score. Thus all the information on risk appears to be contained in the Disease Score. As seen from FIG. 8, the Disease Scores significantly out-performs Framingham and a model including both the Disease Score and the Framingham Score did not improve on the Disease Score itself.[20]

Discussion

The traditional approach to reduction of risk for cardiovascular disease events has been two-fold: (1) screen the healthy population for "risk factors" and intervene with non-pharmacologic or pharmacologic approaches in those whose measurements are above a level defined as "normal"; and (2) intervene aggressively in those individuals who have suffered from a cardiovascular event with therapy aimed at "secondary prevention".

The fallacies of this approach from both a public health and individual patient standpoint are multiple. The "risk factors" measured, including blood pressure, cholesterol, blood sugar, inflammatory markers, etc., are neither sensitive nor specific for the atherosclerotic disease we are attempting to prevent. Furthermore, the so-called upper limit of normal of these measurements does not separate high from low risk. Indeed, each of these "risk factors" appears to display a continuous, nearly linear relationship between the level and the risk for cardiovascular events.[21] Thus, the risk for progression in individuals with demonstrable vascular disease is now recognized to be influenced even by "normal" levels of these risk factors. This insight has led to the recommendation of lipid lowering therapy in all patients who have sustained a coronary event, regardless of their cholesterol level, and the lowering of the threshold for blood pressure treatment in those with diabetes and vascular disease.

The fallacy of waiting for an event to occur before initiating aggressive secondary preventive therapy is obvious. Events usually occur in individuals with advanced disease. They are costly to the health care system and the well being of our patients. They portend a high risk for subsequent events and a shortened life expectancy.

The costs of future management of patients who have sustained an event are considerable. It is intuitive that interventions aimed at preventing progression in early, asymptomatic disease would yield a healthier population and a reduction in health care costs. Despite the clear advantages of this approach, little effort has been expended to develop comprehensive screening programs to detect early disease so that aggressive preventive efforts can be mounted.

Accordingly, there appears to be a need or demand for a community-oriented facility to undertake this effort. Among the first 613 asymptomatic individuals screened and monitored for outcomes in our Minneapolis center, nearly 40% exhibited advancing disease in need of treatment because of a high morbid event rate. Since all of these individuals were in a high socioeconomic group with health insurance and access to primary care physicians, it is clear that our health care system is not providing adequate management to identify and treat high risk individuals. Furthermore, because these individuals did not exhibit organ system symptoms that might have precipitated referral to a cardiovascular specialist, the burden of diagnosis and treatment must fall on the primary care physician.

According to one embodiment, a community testing center uses a specialized, nurse-practitioner managed screening program using state-of-the-art methodology not generally available in the primary care setting that empowers primary care physicians with data and recommendations that can be incorporated into their care of those individuals screened. The modest cost of the screening visit should be returned many times over by the prevention or delay in development of costly cardiovascular events.

The procedures utilized to screen for early vascular and cardiac disease in such a community center are, in one embodiment, selected based upon current published experience with many of the tests and physiologic concepts that led to the development of others. According to this philosophy, early disease rather than abnormal risk factors is the focus of therapeutic intervention. Indeed, the distinction between normal and abnormal values for risk factor assessment loses its meaning when early disease is present. In a treatment center of the present invention, treatment of even so-called normal levels of blood pressure and cholesterol are recommended. In the absence of evidence for vascular or cardiac disease, it is likely—although not yet proven—that events will not occur prematurely. Since management strategies in the present era at best delay further events, and since individuals without early disease may eventually develop disease and events in their later years, the economic burden of health care for cardiovascular events may merely be shifted to an older age. Thus, critical to the overall goal of reducing health care costs might be a societal decision regarding the upper age at which aggressive and expensive medical care is provided.

The scoring system described herein represents an effort to quantitate the evidence for early vascular or cardiac disease likely to progress to morbid events. According to one example embodiment, it is a hypothesis that the higher the score the greater likelihood a cardiovascular event will occur. Interventions aimed at risk contributors, such as blood pressure and cholesterol, should reduce the event rate but only in individuals at risk. Indeed, such therapy-induced risk reduction may in part obscure the relationship between Disease Score and future event rate. According to yet another example embodiment, the aggressiveness of primary care physicians in following testing recommendations provided to them are another variable that must be monitored.

In one other example embodiment, an abnormal test result is assigned a score of 2, a borderline abnormal test a score of 1, and a normal test a score of 0. Therefore, a maximum abnormal score is 20, and a perfectly normal score is zero. The tests administered are: (1) large artery elasticity, (2) small artery elasticity, (3) blood pressure at rest, (4) blood pressure during exercise, (5) retinal arteries (Optic fundus photo), (6) microalbuminuria requiring urine for microalbumin, (7) large artery disease (carotid ultrasound for wall thickness, previously ankle-bracial index), (8) electrocardiogram, (9) BNP blood assay, (10) left ventricular ultrasound. A total score of 6 or greater has been identified as indicative of significant disease in need of therapy/treatment. In an embodiment, a score of three or above indicates likelihood of early disease and in need of therapy/treatment.

In various embodiments, a multi-stage testing procedure is used on a patient. As used herein, the term patient is used generically to refer to the person that the tests are being performed upon and is not limited to persons that have established a doctor/patient relationship. In an example embodiment, the multi-stage testing procedure is used to minimize the amount of tests performed on the patient. For example, consider ten tests that may be performed on the patient to help determine the risk of cardiovascular disease. An initial set of four tests may be performed and scored. If the score is below a threshold, the remaining six tests may not be performed on the patient. If the score is at or above the threshold, the remaining tests are performed and scored. In various embodiments, the tests are a closed set (e.g., only a set number of tests is performed).

In various embodiments, an initial set of four tests may be performed on the patient and scored to determine an initial score. The initial score may be generated according to the numbers and figures previously discussed. Thus, each test in the set of tests may receive a score on a point scale selected from the group consisting of 0, normal; 1, borderline abnormal, or 2, abnormal. Thus a total score for the 4 tests may range from 0 to 8, but other scales may be used.

In an embodiment, the initial score may be compared against a threshold score. If the patients scores above the threshold, the remaining six tests are performed on the patient. In various embodiments, the threshold score may be based on analyzing previously conducted assessments that used all ten tests. For example, as described above in the analysis of 1806 patients, using a threshold of three may mean that more than 60% of tested patients may be excluded from undergoing the entire ten-test assessment. Other thresholds may be used to include or exclude more patients from performing the entire ten-test assessment.

In an example embodiment, the initial four tests are the following: the measurement of resting blood pressure of the patient; the measurement of the change in blood pressure in response to three minutes of a patient exercise on a treadmill adjusted for a work load of 5 METS (metabolic equivalents); and the measurement of small artery and large artery elasticity with a transducer applied to the wrist using, for example, a CVPROFILOR® instrument.

In an embodiment, the four tests are scored as discussed above and if the score is below a three, the patient does not undergo any further tests. If the total score of all four tests is at or above a three, the six remaining tests are performed on the patient. In an embodiment, the six remaining tests are the following: imaging the optic fundus; analyzing a spot urine sample for albumin excretion; a carotid ultrasound; an electrocardiogram; a BNP blood assay; and a left ventricular ultrasound.

In an embodiment, all six remaining tests are performed and scored according to the figures and discussion above. In an embodiment, the total score of the remaining tests is added to the total score from the initial four tests to determine a disease score. If the disease score is six or above, the patient may be informed that the patient's disease score is indicative of significant disease and that the patient is in need of therapy/treatment. A patient whose disease score is between three and five, inclusive, may be informed that the patient's score indicates a likelihood of early disease and the patient is in need of therapy/treatment. A patient whose disease score is less than three may be informed that the patient's score indicates a low likelihood of disease, but that the patient should be periodically (e.g., every five years) re-tested.

Figure 9:
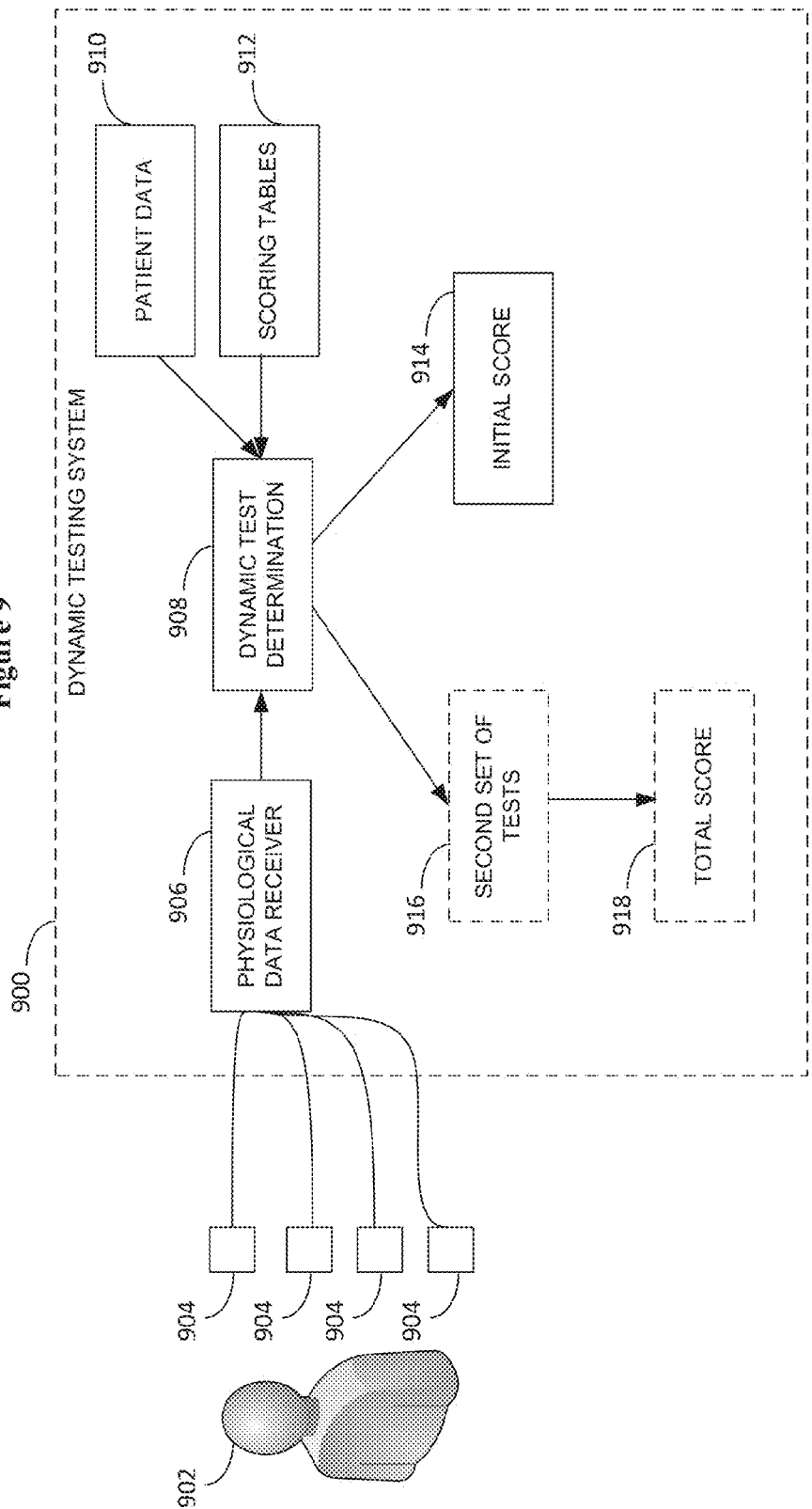
FIG. 9 is a diagram of a dynamic testing system, according to an example embodiment.

FIG. 9 is a diagram of a dynamic testing system according to example embodiment. Illustrated is dynamic testing system 900, patient 902, medical devices 904, physiological data receiver 906, dynamic test determination component 908, patient data 910, scoring tables 912, initial score 914, second set of tests 916, and total score 918.

In various embodiments, one or more apparatuses may be used in dynamic testing system 900 to assist the person (e.g., nurse practitioner, practitioner helper, doctor, tester, etc.) conduct the tests on patient 902. The assistance may include determining which tests to perform, performing the tests, scoring the tests, and recommending courses of actions to the patient.

For example, a testing assistance device (not shown) may include an output device, a network interface, an input device, a processor (e.g., a general purpose processor or application specific integrating circuit (ASIC)), a storage device, and one or more I/O ports for connecting to external devices (e.g., medical equipment). Example assistance devices include personal computers, limited purpose computers (e.g., kiosks), or mobile devices (e.g., phones, tablets, cellular phones). The assistance device may include more than input device, output device, network interface, and storage device.

In various embodiment, an input device includes, but is not limited to, a mouse, touch screen, keyboard, microphone, motion capture device (e.g., camera, sensors for use in capturing gestures), or accelerometer. An output device may include a display screen, touch screen, haptic feedback device, or audio device. In various embodiments, the network interface may be a wired (e.g., Ethernet) or wireless (e.g., radio based).

The storage device may include instructions, that when executed by the processor, configure the computer to display a testing assistance application. Additionally, the storage device may store patient data 910 (e.g., medical and demographic records), threshold data, scoring tables 912, and testing procedures in a database (e.g., flat file, relational).

The testing application may help a testing practitioner through performing the multi-stage testing on one or more patients. For example, upon opening the application on the assistance device a testing practitioner may be presented, on an output device, instructions (e.g., video, photo, textual, audio) for an intake procedure for the patient. This may include asking the patient personal information (e.g., name, date of birth) and any known health risks. If the patient already exists in the database, a record of the patient in the database may be updated. If the patient is new, a new patient record may be generated and stored in the database.

In an example embodiment, upon completing the intake procedure the practitioner may be presented with instructions to perform one of the first set of tests in the multi-test assessment according to data stored in the database. For example, the instructions may say, "Take a measurement of the resting blood pressure of the patient."

In various embodiments, one or more medical devices 904 are connected to the assistance device to perform the initial four tests. Physiological data (e.g., blood pressure reading) for each test may then be inputted into the dynamic testing system and stored in digital form. For example, if a medical device is connected to the assistance device, the physiological data associated with the test result may be received directly in the assistance device and translated from an analog measurement to digital as necessary. If the measurement is taken by the health practitioner manually, the result may entered into the assistance device (e.g., via a GUI form).

In an embodiment, dynamic test determination component 908 takes the digital physiological data for a test and correlates it to the corresponding readings in scoring tables 912 to determine a score. In an embodiment, dynamic test determination component 908 is executed on the testing assistance device. The testing application may guide the testing practitioner through the initial four tests in the first stage and obtain a score for each. In various embodiments, the order of the tests may be stored in the application or separate file on the assistance device and may be updated as needed (e.g., via an update received over the network interface).

In an example embodiment, the testing application, through the use of dynamic test determination component 908, calculates initial four-test score 914 for the patient. In an embodiment, dynamic test determination component 908 compares initial score 914 to a threshold. If the initial score is below a threshold (e.g., as stored in the database or with the application), the testing application may instruct the testing practitioner to not perform any further tests and to inform the patient that the patient shows little signs of cardiovascular disease.

In an embodiment, if the initial score is at or above the threshold, dynamic test termination component 908 determines second set of tests 916. In an embodiment, second set of tests 916 may be the remaining six tests. Thus, the testing application may guide the testing practitioner through the remaining tests. In various embodiments, the health record of the patient is updated with the results of the tests. In an embodiment, the second set of tests are performed by a different individual than the person who conducted the initial four tests. In an embodiment, dynamic test determination component 908 may use patient data 910 to determine that not all of the remaining tests need to be performed. For example, the patient record data may already have results for one or more of the remaining tests. Thus, dynamic test determination component 908 may use the results and data in scoring tables 912 to determine a score without subjecting the patient to the test again. This may be determined based on how recent the test was completed. For example, if the results of the previously test were completed within a week of the initial four tests, the previously conducted test may be excluded from the second set of tests. Additionally, dynamic test determination component 908 may determine that the demographics of the patient indicate that one or more of the six remaining tests should not be performed.

In various embodiments, upon completing the entire ten-test assessment (or subset of tests as determined by dynamic test determination component 908), the testing application computes a total disease score 918 for the patient. In an embodiment, the total disease score is a score from 0-20 based on the sum of the individual scores of the ten tests. If the disease score is above a threshold, the testing application may instruct the testing practitioner to inform the patient that the patient shows signs of significant cardiovascular disease. If the disease score is at or below the threshold the patient may be informed that the patient shows signs that indicate early disease.

The testing application may also present one or more contacts that the patient may contact for therapy/treatment. In an embodiment, a drug may be prescribed/administered to the patient if disease is likely present based on a comparison of the disease score to the threshold. For example, a drug to treat hypertension may be administered to the testing subject or a drug to treat high cholesterol. In various embodiments, diet changes may also be recommended to the patient. When a drug is administered or diet change recommended, an entry in the database may be generated and associated with the patient for tracking or later retrieval.

In various embodiments, the assistance device is a thin terminal that connects, via the network interface, to a server that hosts the application. Thus, little to no health data is stored (or only is temporarily) at the assistance device. For example, medical records and results of the testing may be stored at the server or another location.

Although the specification has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. This disclosure is intended to cover any and all adaptations or variations of various embodiments. Combinations of the above embodiments, and other embodiments not specifically described herein, will be apparent to those of skill in the art upon reviewing the above description.

REFERENCES

1. Grundy S M, Balady G J, Criqui M H, (complete authors). Primary prevention of coronary heart disease: guidance from Framingham. Circulation 1998; 97: 1876-87.
2. Downs J R, Clearfield M, Weis S, Whitney E, Shapiro D R, Beere P A, Langendorfer A, Stein E A, Kruyer W, Gotto A M Jr. Primary prevention of acute coronary events with lovastatin in men and women with average cholesterol levels: results of AFCAPS/TexCAPS. Air Force/Texas Coronary Atherosclerosis Prevention study. JAMA 1998; 279:1615-22.
3. Antiplatelet Trialists Collaboration. Secondary prevention of vascular disease by prolonged antiplatelet therapy. BMJ 1988; 296-331.
4. Gottlieb S S, McCarter R J, Vogel R A. Effect of beta-blockade on mortality among high risk and low-risk patients after myocardial infarction. N EngL J Med 1998; 339:489-97.
5. Scandinavian Simvastatin Survival Study Group. Randomised trial of cholesterol lowering in 4444 patients with cornary heart disease: the Scandinavian Survival Study (4S). Lancet 1994;344:1383-9.
6. Long-term Intervention with Pravastatin in Ischemic Disease (LIPID) Study Group. Prevention of cardiovascular events and death with pravastatin in patients with coronary heart disease and a broad range of initial cholesterol levels. The Long-term Intervention with Pravastatin in Ischaemic Disease (LIPID) Study Group. N Engl J Med 1998;339: 1349-57.
7. Clarke R, Daly L. Robinson K, Naughten E, Cahalane S, Fowler B, Graham I. Hyperhomocysteinemia: an independent risk factor for vascular disease. N Engl J Med 1991; 324:1149-55.
8. Stein I I Rosenson R S. Lipoprotein Lp(a) excess and coronary heart disease. Arch Intern Med 1997;157:1170-6.
9. Kannel W B. Blood pressure as a cardiovascular risk factor. JAMA 1996;275:1571-76.
10. Ridker P M, Glynn R J, Hennekens C H. C-reactive protein adds to the predictive value of total and HDL cholesterol in determining risk of first myocardial infarction. Circulation 1998;97:2007-11.
11. The SOLVD Investigators. Effect of enalapril on mortality and the development of heart failure in asymptomatic patients with reduced left ventricular ejection fractions. N Engl J Med 1992;327:685-91.
12. Yusuf S, Sleight P, Pogue J, Bosch J, Davies R, Dagenais G. Effects of an angiotensin-converting-enzyme inhibitor, ramipril, on cardiovascular events in high-risk patients. The Heart Outcomes Prevention Evaluation Study Investigators. N Engl J Med 2000;342:145-53.
13. Effect of metroprolol CR/XL in chronic heart failure: Metroprolol CR/XL. Randomised Intervention Trial in Congestive Heart Failure (MERIT-HF). Lancet 1999;353: 2001-7.
14. Ross R. The pathogenesis of atherosclerosis: a perspective for the 1990's. Nature 1993;362:801-9.
15. Cohn J N, Finkelstein S, McVeigh G, Morgan D, LeMay L, Robinson J, Mock J. Non-invasive pulse wave analysis for the detection of arterial vascular disease. Hypertension 1995;26:503-8.
16. Lim P O, Shiels P, Anderson J, MacDonald T M. Dundee step test: a simple method of measuring the blood pressure response to exercise. J Human Hypertens 1999;13:521-6.
17. Borch-Johnsen K, Feldt-Rasmussen B, Strandgaard S, Schroll M, Jensen J S. Urinary albumin excretion. An independent predictor of ischemic heart disease. Arteriosclerosis, Thrombosis & Vascular Bio 1999;19:1992-7.
18. Duprez D A, Cohn J N. Identifying early cardiovascular disease to target candidates for treatment. J Clin Hypertension 2008; 10(3):226-231.
19. Maisel A S, Koon J, Krishnaswamy P, Kazenegra R, Clopton P, Gardetto N, Morrisey R, Garcia A, Chiu A, DeMaria A. Utility of B-natriuretic peptide as a rapid, point-of care test for screening patients undergoing echocardiography to determine left ventricular dysfunction. Am Heart J 2001;141:367-74.
20. Duprez D A, Florea N, Zhong W, Grandits G A, Hawthorne C K, Hoke L, Cohn J N. Vascular and cardiac functional and structural screening to identify risk of future morbid events: preliminary observations. J Amer Soc Hypertens 2011;5:401-409.
21. Cohn J N. Arteries, myocardium, blood pressure and cardiovascular risk: towards a revised definition of hypertension. Jrnl Hypertension 1998;16:2117-24.

What is claimed is:
1. A system comprising:
at least one processor;
a storage device with instructions stored thereon, wherein the instructions when executed on the at least one processor configure the at least one processor to:
receive physiological data resulting from a first set of tests performed on a subject in a first stage of testing, the first stage consisting of:
measuring the resting blood pressure of the subject;
measuring a change in the blood pressure after the subject has performed an exercise;
measuring small artery elasticity of the subject; and
measuring large artery elasticity of the subject;
receive physiological results for each of the tests in the first stage;
score each of the tests in the first stage of testing based on the physiological results to determine an initial score of the subject;
based in part on a comparison between the initial score and a threshold, dynamically determine a set of tests to perform on the subject in a second stage of testing, the set of tests in the second stage of testing selected from the group consisting of:
imaging the optic fundus of the subject;
performing an ultrasound of both carotid arteries
analyzing a spot urine sample of the subject for albumin excretion;
performing an electrocardiogram on the subject;
performing a BNP blood assay on the subject; and
performing a left ventricular ultrasound on the subject;
receive physiological data resulting from performing the set of tests on the subject in the second stage of testing.
2. The system of claim 1, wherein the instructions further configure the at least one processor to:
retrieve a patient record for the subject from a database, the patient record indicating a physiological result of a test previously performed on the subject; and
dynamically determine the set of tests to perform on the subject in the second stage of testing based in part on the patient record.
3. The system of claim 2, wherein the instructions further configure the at least one processor to:
exclude a test from the second stage of testing when the test previously performed on the subject was performed within a predetermined time period of the first stage of testing.
4. The system of claim 1, further comprising a database configured to store an entry associated with the subject, the entry includes a disease score based on the initial score and a score of the second stage of testing and the entry including data indicating a drug administration to the subject based on the disease score.

5. A multi-stage method of predicting or detecting cardiovascular ailments in a subject, the method comprising:
performing a first set of tests in a first stage of testing on the subject, the first stage consisting of:
measuring the resting blood pressure of the subject;
measuring a change in the blood pressure after the subject has performed a standardized exercise on a treadmill;
measuring small artery elasticity of the subject; and
measuring large artery elasticity of the subject;
receiving physiological results for each of the tests in the first stage and a computer-generated interpretation of each of the tests as normal, borderline, or abnormal based in part on age and gender-specific criteria for normalcy;
scoring, using at least one processor, each of the tests in the first stage of testing based on the physiological results to determine an initial score of the subject;
comparing, using the at least one processor, the initial score to a threshold;
based on the comparison to the threshold, dynamically determining a set of tests to perform on the subject in a second stage of testing, the set of tests selected from the group consisting of:
imaging the optic fundus of the subject;
performing an ultrasound of both carotid arteries;
analyzing a spot urine sample of the subject for albumin excretion;
performing an electrocardiogram on the subject;
performing a BNP blood assay on the subject; and
performing a left ventricular ultrasound on the subject;
performing the dynamically determined set of tests in the second stage of testing.

6. The method of claim 5 further comprising:
including all of the tests in the group in the dynamically determined set of tests when the initial score is at or above the threshold.

7. The method of claim 5 further comprising:
including none of the tests in the group in the dynamically determined set of tests when the initial score is below the threshold.

8. The method of claim 5, wherein scoring each of the tests in the first stage of testing to determine an initial score of the subject comprises:
translating the received physiological data to a digital form;
correlating the digital form of the physiological data to data in a scoring table; and
based on the correlation, scoring each test with a number selected from the group consisting of 0, 1, and 2.

9. The method of claim 5, further comprising:
retrieving a patient record for the subject from a database, the patient record indicating a physiological result of a test previously performed on the subject; and
dynamically determining the set of tests to perform on the subject in the second stage of testing based in part on the patient record.

10. The method of claim 5, wherein dynamically determining a set of tests to perform on the subject in a second stage of testing comprises:
excluding a test from the second stage of testing when the test was previously performed on the subject within a predetermined time period of the first stage of testing.

11. A computer-readable storage device storing instructions, that when executed by at least one processor, cause the at least one processor to:
receive physiological data resulting from a first set of tests performed on a subject in a first stage of testing, the first stage consisting of:
measuring the resting blood pressure of the subject;
measuring a change in the blood pressure after the subject has performed an exercise;
measuring small artery elasticity of the subject; and
measuring large artery elasticity of the subject;
receiving physiological results for each of the tests in the first stage;
scoring each of the tests in the first stage of testing based on the received physiological results to determine an initial score of the subject;
comparing the initial score to a threshold;
based in part on the comparing, dynamically determine a set of tests to perform on the subject in a second stage of testing, the set of tests selected from the group consisting of:
imaging the optic fundus of the subject;
performing an ultrasound of both carotid arteries analyzing a spot urine sample of the subject for albumin excretion;
performing an electrocardiogram on the subject;
performing a BNP blood assay on the subject; and
performing a left ventricular ultrasound on the subject;
receive physiological data resulting from performing the set of tests on the subject in the second stage of testing.

12. The storage device of claim 11 further comprising:
including all of the tests in the group dynamically determined set of tests when the initial score is at or above the threshold.

13. The storage device of claim 11 further comprising:
including none of the tests in the group dynamically determined set of tests when the initial score is below the threshold.

14. The storage device of claim 11, wherein scoring each of the tests in the first stage of testing to determine an initial score of the subject comprises:
translating the received physiological data to a digital form;
correlating the digital form of the physiological data to data in a scoring table; and
based on the correlation, scoring each test with a number selected from the group consisting of 0, 1, and 2.

15. A multi-stage method of predicting or detecting cardiovascular ailments in a subject, the method comprising:
performing a first set of tests in a first stage of testing on the subject, the first stage consisting of:
measuring the resting blood pressure of the subject;
measuring a change in the blood pressure after the subject has performed an exercise;
measuring small artery elasticity of the subject; and
measuring large artery elasticity of the subject;
receiving physiological results for each of the tests in the first stage;
individually scoring, using at least one processor, each of the tests in the first stage based on the received physiological results of tests in the first stage;
based on the sum of the individual scores being above a threshold, performing a second set of tests in a second stage of testing on the subject, the second stage consisting of:
imaging the optic fundus of the subject;
performing an ultrasound of both carotid arteries analyzing a spot urine sample of the subject for albumin excretion;
performing an electrocardiogram on the subject;
performing a BNP blood assay on the subject; and
performing a left ventricular ultrasound on the subject;

receiving physiological results for each of the tests in the second stage;
individually scoring each of the tests in second stage based on the received physiological results of tests in the second stage; and
calculating, using the at least one hardware processor, a disease score based on the sum of the individual scores of the tests in the first stage and the individual scores of the tests performed in the second stage.

16. The method of claim 15, further comprising:
administering a drug to treat hypertension when the disease score is above a determined threshold.

* * * * *